(12) United States Patent
Thiberg

(10) Patent No.: US 6,537,303 B1
(45) Date of Patent: Mar. 25, 2003

(54) METHOD FOR TREATMENT OF MAMMALS

(75) Inventor: Rolf Thiberg, Åkersberga (SE)

(73) Assignee: Biolight Patent Holding AG, Danderyd (SE)

( * ) Notice: Subject to any disclaimer, the term of this patent is extended or adjusted under 35 U.S.C. 154(b) by 0 days.

(21) Appl. No.: 09/972,770

(22) Filed: Oct. 7, 2001

(51) Int. Cl.7 .............................................. A61N 33/00
(52) U.S. Cl. ............................ 607/88; 607/89; 128/898
(58) Field of Search ....................... 607/88, 89; 128/898

(56) References Cited

U.S. PATENT DOCUMENTS

| | | | |
|---|---|---|---|
| 4,976,263 A * | 12/1990 | Seidl et al. .................... | 607/63 |
| 5,766,233 A | 6/1998 | Thiberg ........................ | 607/88 |
| 5,800,479 A | 9/1998 | Thiberg ........................ | 607/88 |
| D441,456 S | 5/2001 | Thiberg ..................... | D24/210 |
| 6,238,424 B1 | 5/2001 | Thiberg ........................ | 607/88 |
| 6,238,425 B1 | 5/2001 | Thiberg ........................ | 607/88 |
| 2002/0111656 A1 * | 8/2002 | Lach ........................... | 607/89 |

* cited by examiner

*Primary Examiner*—Roy D. Gibson
*Assistant Examiner*—Henry M Johnson, III
(74) *Attorney, Agent, or Firm*—Alfred J. Mangels

(57) ABSTRACT

A method for treatment of mammals by draining lymph along a lymph pathway within a mammal's body. An infrared-light-emitting device is utilized to emit pulsating infrared light at a low pulse repetition frequency. The light-emitting device is brought into contact with the body and is moved along a lymph pathway in a direction toward the lymphatic gland to which the pathway of the lymph vessel in question leads.

8 Claims, 1 Drawing Sheet

METHOD FOR TREATMENT OF MAMMALS

BACKGROUND OF THE INVENTION

1. Field of the Invention

The present invention relates to a method for treatment of mammals by draining lymph. More particularly, the present invention relates to a method of draining lymph by the application of pulsating light to the body.

2. Description of the Related Art

Lymph is a viscous liquid, i.e., blood plasma, which transports nutritional substances to the cells in the body and drains waste products from the cells. Sometimes lymph circulation is disturbed or interrupted, which may lead to cells dying.

Until recently, drainage of lymph was performed manually in order to help the circulation of lymph within the human body. Drainage of lymph is performed using light pump-like massage movements over the body. Such movements are circle-like or have a spiral shape. By those movements one tries to drive the lymph in a correct flow direction. By influencing the transport of lymph in a positive way, waste products within the body can be removed faster.

It is considered especially important that excess proteins in cell membranes be removed, because such proteins bind liquid to the body, with the result that the body swells up.

The drainage of lymph also influences the autonomous nervous system and provides a state of comfort in a patient.

The inventor of the present invention has developed an apparatus for transmitting monochromatic light for medical treatment of the body. That apparatus and its use and benefits are described in U.S. Pat. No. 5,766,233, entitled "Device for Wound Healing by Means of Light," which issued on Jun. 16, 1998, to Rolf Thiberg; U.S. Pat. No. 5,800,479, entitled "Device for Medical External Treatment by Means of Light, which issued on Sep. 1, 1998, to Rolf Thiberg; U.S. Pat. No. D441,456 S, entitled "Skin Treatment Lamp," which issued on May 1, 2001, to Rolf Thiberg; U.S. Pat. No. 6,238,424 B1, entitled "Device for External Treatment with Pulsating Light of High Duty Cycle," which issued on May 29, 2001, to Rolf Thiberg; and U.S. Pat. No. 6,238,425 B1, entitled "Device for External Medical Treatment with Monochromatic Light," which issued on May 29, 2001, to Rolf Thiberg. That treatment device has been used for treatment of wounds and pain in humans and animals. The monochromatic light is transmitted with a certain pulse repetition frequency and with a duty cycle of from about 60% to about 90%.

It has now surprisingly been discovered that a treatment using monochromatic light can be successfully employed for lymph drainage.

SUMMARY OF THE INVENTION

The present invention thus relates to a method for draining lymph from the human or animal body by the use of a device that emits pulsating light. The device emits pulsating infrared light that pulses at a low pulse repetition frequency. In use, the light-emitting device is brought into contact with the body and is moved along the pathways of the lymph flow in a direction toward the lymphatic gland to which the pathway of the lymph vessel in question leads.

BRIEF DESCRIPTION OF THE DRAWINGS

The present invention will be described in greater detail hereinafter using exemplifying embodiments of the invention and the accompanying drawings in which.

DESCRIPTION OF THE PREFERRED EMBODIMENTS

Figures 1, 2:
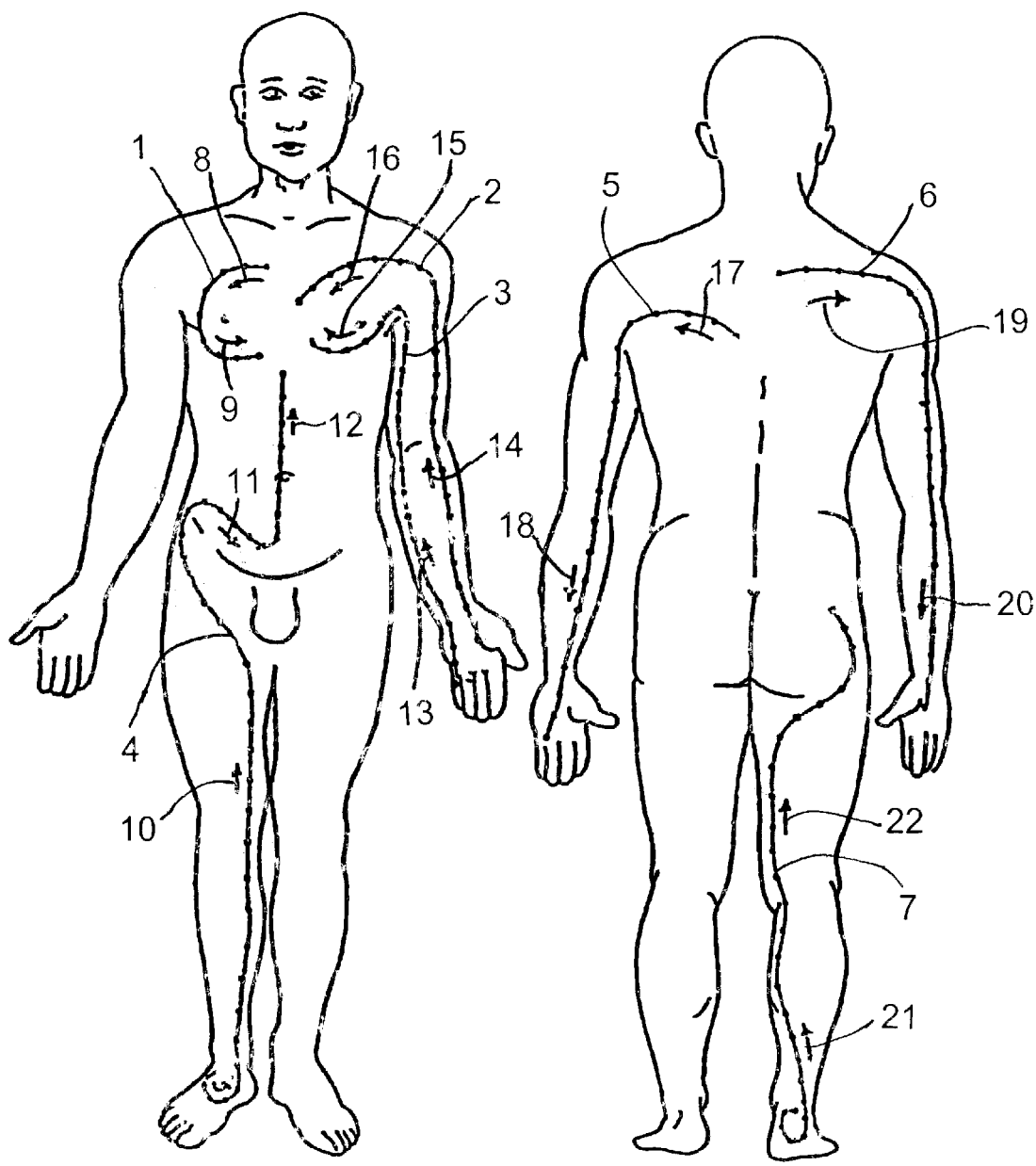
FIG. 1 shows a front view of the human body and certain pathways of lymph vessels.
FIG. 2 shows a rear view of the human body and certain pathways of lymph vessels.

In FIGS. 1 and 2 several lymph pathways are designated by respective reference numerals 1 through 7. In that regard, it is to be understood that the pathways shown in FIGS. 1 and 2 are only a few exemplifying lymph pathways among all the lymph pathways that exist.

In accordance with the present invention, a light-emitting device (not shown), is first brought into contact with the body and then is slowly moved along a lymph pathway in a direction toward the lymphatic gland to which the pathway of the lymph vessel in question leads. The directions of movement for each of the lymph pathways shown in the drawings are indicated by the respective arrows designated by reference numerals 8 through 22.

The light-emitting device utilized in carrying out the present invention can be of the type, structure, and method of operation as disclosed in the inventor's previously-issued U.S. patents identified above. In that regard, the entire disclosure of each of those patents is hereby incorporated by reference herein to the same extent as if fully rewritten herein.

According to a preferred embodiment of the invention, the light-emitting device is brought into contact with the surface of the body at a location adjacent to or overlying the beginning of a lymph pathway that ends at a lymphatic gland. The speed of the movement of the light-emitting device should be rather slow. As an example, the movement along a person's leg should take about 20 seconds. The combination of the slow speed movement of the device and the pulse repetition results in a pump-like effect on the lymph.

According to another preferred embodiment, a specific area of the body that is injured is locally treated by applying the light-emitting device to the injured area after a general treatment of the injured area has been carried out by slowly moving the device along the lymph pathway adjacent to or associated with that injured area.

According to a further preferred embodiment of the invention, the light-emitting device is caused to emit pulsed infrared light with a pulse repetition frequency of about 7.8+/−1 Hz or about 15.6+/−1.3 Hz, depending upon the type of treatment intended. In that connection, the higher pulse repetition frequency gives a milder treatment, and it can be used to treat stiffness after training, for example. Swollen areas can be treated using the lower pulse repetition frequency.

According to another preferred embodiment of the invention, the light-emitting device is caused to emit infrared light having a wavelength of about 950+/−20 nanometers. Infrared light of such a wavelength penetrates the skin to a deepest level of about 30 millimeters.

It is important to observe that the emitted light should not be caused to rotate about an axis that is perpendicular to the body surface overlying the body part in question, as has been used previously for many other light treatment methods.

The above-mentioned treatment method has been utilized in several studies. The method of use and the results obtained from practicing the treatment method in accordance with the present invention will now be illustrated by one case study.

A world-class female athlete had been stricken with breast cancer. After undergoing surgery a substantial swelling arose in her right arm. Manual drainage by using pump-like massage movements was not possible because of pain. A light-emitting device obtained from Biolight International AB, Sweden (designated Biolight Model PCD) was utilized to cause lymph drainage from the arm. The light pulse repetition frequency was set to 7.8 Hz and the duty cycle at 80%. The device was slowly moved from the athlete's wrist to her armpit over a time span of 30 seconds. That procedure was repeated 20 times. The lymph drainage procedure was performed in the morning and in the evening. After three days of such treatment the swelling was eliminated and the athlete's arm was entirely normal in size.

After recovery from the cancer surgery the athlete started her training, which unfortunately resulted in severe pain in her legs due to lactic acid. The same light-emitting device as was used before in connection with the swelling in her arm was now used to drain lymph from the legs, to take the waste products away. The light pulse repetition frequency was set to 15.6 Hz and the duty cycle at 80%. The device was slowly moved from the athlete's ankle to her inguinal region over a time span of 60 seconds. That treatment was repeated 10 times on each leg. The following day the pain was gone and the athlete could train again. The treatment procedure utilizing the light-emitting device was perceived by the athlete as a significant contrast to the earlier-used procedure involving manual drainage, because it was much quicker and was totally without pain.

In the foregoing description certain exemplifying methods have been described. However it is apparent that the present method is not limited to those examples, but may vary within the scope of the patent claims. Consequently, although particular embodiments of the present invention have been illustrated and described, it will be apparent to those skilled in the art that various changes and modifications can be made without departing from the spirit of the present invention. Accordingly, it is intended to encompass within the appended claims all such changes and modifications that fall within the scope of the present invention.

What is claimed is:

1. A method for treatment of mammals by inducing lymph flow within a mammal body, said method comprising the steps of:

providing a source of infrared light;

pulsating the infrared light in accordance with a predetermined pulse repetition frequency;

directing the source of pulsating infrared light against the mammal body; and moving the source of pulsating infrared light in a direction corresponding with a direction of a lymph pathway that is within the body and toward a lymphatic gland to which the lymph pathway leads.

2. A method according to claim 1, wherein the source of pulsating infrared light is directed at a location corresponding with the beginning of a lymph pathway that ends at a lymphatic gland.

3. A method according to claim 2, including the step of locally treating a specific area of the body by exposing that area to the source of pulsating infrared light.

4. A method according to claim 1, wherein the pulse repetition frequency is about 7.8+/-1 Hz.

5. A method according to claim 1, wherein the pulse repetition frequency is about 15.6+/-1.3 Hz.

6. A method according to claim 1, wherein the source of pulsating infrared light emits infrared light having a wavelength of about 950+/-20 nanometers.

7. A method according to claim 4, wherein the source of pulsating infrared light emits infrared light having a wavelength of about 950+/-20 nanometers.

8. A method according to claim 5, wherein the source of pulsating infrared light emits infrared light having a wavelength of about 950+/-20 nanometers.

* * * * *

UNITED STATES PATENT AND TRADEMARK OFFICE
CERTIFICATE OF CORRECTION

PATENT NO. : 6,537,303 B1
DATED : March 25, 2003
INVENTOR(S) : Rolf Thiberg

It is certified that error appears in the above-identified patent and that said Letters Patent is hereby corrected as shown below:

<u>Title page,</u>
Item [73], Assignee, should read:
-- [73] Assignee: Biolight Patent Holding AB --

Signed and Sealed this

Twenty-second Day of July, 2003

JAMES E. ROGAN
*Director of the United States Patent and Trademark Office*